United States Patent [19]

Okorodudu

[11] Patent Number: 4,826,629
[45] Date of Patent: May 2, 1989

[54] NON-METALLIC MULTIFUNCTIONAL LUBRICANT ADDITIVES AND COMPOSITIONS THEREOF

[75] Inventor: Abraham O. M. Okorodudu, West Deptford, N.J.

[73] Assignee: Mobil Oil Corporation, New York, N.Y.

[21] Appl. No.: 40,658

[22] Filed: Apr. 20, 1987

[51] Int. Cl.$^4$ .......................................... C10M 137/04
[52] U.S. Cl. .............................. 252/32.7 E; 252/46.6; 558/161
[58] Field of Search .................... 252/46.6, 32.7 E; 558/161

[56] References Cited

U.S. PATENT DOCUMENTS

| | | | |
|---|---|---|---|
| 2,343,831 | 3/1944 | Osborne | 252/46.6 |
| 2,443,264 | 6/1948 | Mikeska | 252/46.6 |
| 2,526,497 | 10/1950 | Mikeska | 252/46.6 |
| 3,346,549 | 10/1967 | Ford et al. | 252/48.4 |
| 3,687,848 | 8/1972 | Colclough | 252/46.6 |

FOREIGN PATENT DOCUMENTS

3616464  8/1963  Japan.

Primary Examiner—William R. Dixon, Jr.
Assistant Examiner—Jerry D. Johnson
Attorney, Agent, or Firm—Alexander J. McKillop; Charles J. Speciale; Howard M. Flournoy

[57] ABSTRACT

Multifunctional (antiwear/anitoxidant) additives prepared by reaction of diorganophosphorodithioic acids and a sulfurous-oxyhalide, e.g. thionyl chloride impart resistance to oxidation and abrasion when incorporated into lubricating oils.

18 Claims, No Drawings

NON-METALLIC MULTIFUNCTIONAL LUBRICANT ADDITIVES AND COMPOSITIONS THEREOF

BACKGROUND OF THE INVENTION

This application is directed to multifunctional lubricant additives prepared by reaction of diorganophosphorodithioic acids and sulfurous oxyhalides, e.g., thionyl chloride which when incorporated into lubricating oils or greases, impart resistance to oxidation and abrasion and increase their service life. These materials are effective in hydrocarbon and synthetic, e.g., ester base stocks.

Zinc dithiophosphates (ZnDTP) have been used for several years in lubricating oils to which they impart multifunctional antiwear/antioxidant protection. However, in recent years, environmental and toxicological demands have created a need for their replacement because of disposal problems and deleterious effects on catalytic converters of automobile engines. Consequently, there have been strong efforts in the industry to find replacements for them. Copper salts of phosphorodithioic acids such as phosphorothionyl disulfide are known in the art; see, for example, U.S. Pat. No. 4,582,920. U.S. Pat. No. 4,405,470 discloses it is known to react a diorganodithiophosphoric acid ester with vinyl carboxylate. The product is described as being useful as an antioxidant in lubricants.

U.S. Pat. No. 3,644,206 discloses a product made by reacting a diorganodithiophosphoric acid with a cyclic hindered aldehyde. The product is useful as an antioxidant in various organic fluids.

U.S. Pat. Nos. 4,000,271; 4,405,470 and 4,582,617 disclose various products and compounds of organophosphorus having utility as deodorizers, greases and lubricants. U.S. Pat. No. 4,600,517 discloses grease formulations containing phosphorus and sulfur moieties.

It is one object of this invention to provide novel organic compositions which have improved oxidation stability and antiwear activity. It is a further object of this invention to provide novel compositions which afford protection against oxidation deterioration for organic media to which they have been added. Another object is to provide improved lubricating oil compositions capable of withstanding the oxidizing conditions of modern engines. These and other objects will become apparent from the following disclosure.

The non-metallic, ashless compounds or additive products described herein have shown very good antiwear/antioxidant effectiveness in lubricating oils and have the potential advantage of better compatibility with, and solubility in, a variety of base stocks.

SUMMARY OF THE INVENTION

This invention is directed to products derived from the reaction of organophosphorodithioic acids and sulfurous-oxyhalides. This invention is also directed to lubricant compositions comprising minor amounts of said products and major amounts of oils of lubricating viscosity. The described products are particularly useful in gear oils and similar lubricant compositions.

DESCRIPTION OF PREFERRED EMBODIMENTS

The additive compounds in accordance with the present invention have the following general formula $$[(RO)_2P(S)S]_2SO$$

where R is hydrocarbyl having from 1 to about 32 carbon atoms. "Hydrocarbyl", as used herein, shall mean alkyl, alkenyl, aryl, aralkyl, alkaryl and cycloalkyl, where the aryl portion has 6 to 14 carbon atoms (e.g., phenyl, naphthyl and anthryl). Preferred are $C_1$-$C_8$ alkyl, 2-ethylhexyl and the like; 4-methyl-2-pentyl and the like; oleyl and nonylphenyl.

Generally speaking, the additive compounds (products) are prepared by reacting stoichiometric or molar quantities of a suitable diorganophosphorodithioic acid with a suitable sulfurous-oxyhalide.

The phosphorodithioic acids utilized herein may be easily made by any convenient prior art method. In one embodiment hydrocarbyl phosphorodithioic acid is made by reacting $P_2S_5$ in a hydrocarbon diluent with 4 molar equivalents of a hydrocarbyl alcohol, such as 1-propanol. Any well known hydrocarbyl alcohol or mixture of alcohols can be used. Preferably the hydrocarbyl groups contain 1-30 carbon atoms and more preferably a $C_1$-$C_{20}$ alkyl or $C_6$-$C_{30}$ cycloalkyl substituted cycloalkyl, aryl, aralkyl or aryl groups.

Other useful phosphorus-sulfur components which may be employed can be one or more substances which contain both phosphorus and sulfur and in which phosphorus has a valence of 1 to 5, and sulfur has a valence of 2 to 6. Molecules in which either or both have fractional valences are operable. Useful compounds include: phosporus disulfide ($PS_2$, $P_3S_6$), diphosphorus trisulfide ($P_2S_3$, $P_4S_6$), and diphosphorus pentasulfide ($P_2S_5$, $P_4S_{10}$). $P_2S_5$ is preferred.

The sulfur halide is preferably thionyl chloride or sulfuryl chloride but any suitable sulfur-halide may be used in the process of this invention. Other suitable sulfurized halides include sulfur monochloride, sulfur dichloride.

Preferably the dihydrocarbyl phosphorodithioic acid after suitable preparation as described hereinabove is reacted with the sulfur-halide in a molar ratio of about 2.2:1 to about 2.5:1 and preferably 2.2:1 of acid to halide under ambient conditions of temperature and pressure. Higher pressures may be used if desired. The reaction can be run with or without a solvent. Solvents that may be used include but are not limited to hexane, toluene and similar hydrocarbon solvents. Additionally, basic substances may be used to remove acid formed in the process. Amines such as triethylamine are preferred. The reaction times vary depending upon specific reactants, temperature and pressure, etc.

The products of the invention are used in minor antiwear/antioxidant amounts with a major proportion of a lubricating oil or grease. In geneal, this will amount to from about 0.01% to about 20% and preferably from about 0.05% to about 15% by weight of the total composition. Furthermore, other additives, such as detergents, other antioxidants, and antiwear agents and the like may be present.

The lubricants contemplated for use with the products herein disclosed include mineral and synthetic hydrocarbon oils of lubricating viscosity, mixtures of mineral oils and synthetic oils, including mixtures. The synthetic hydrocarbon oils include long-chain alkanes such as cetanes and olefin polymers such as oligomers of hexene, octene, decene, and dodecene, etc. The products of this invention are especially effective in synthetic oils formulated using mixtures of synthetic hydrocarbon olefin oligomers and lesser amounts of hydrocarbyl carboxylic ester fluids. Other synthetic oils, which can be mixed with a mineral or synthetic hydrocarbon oil, include (1) fully esterified ester oils, with no free hydroxyls, such as pentaerythritol esters of monocarboxylic acids having 2 to 20 carbon atoms, trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids.

Having described the invention with reference to its broader aspects, the following are offered to specifically illustrate it. It will be understood that the Examples are for illustration only and are not intended to limit the scope of the invention.

EXAMPLE (3)

Di-2-ethylhexyl phosphorodithioic acid 1062 g (3 moles) was charged into a 2-liter reaction flask protected from moisture. To this, while stirring, at ambient temperature, thionyl chloride, 180 g (1.5 moles) was added dropwise, maintaining the exothermic reaction temp at $44\pm2°$ C., to control copious HCl evolution. After the addition and the exothermic reaction temperature had subsided, the mixture was heated at 50° C. for four hours while purging with dry $N_2$. The product was then filtered over Hi-flo to give a clear odorless amber oil in 95% yield.

Example 2 was prepared using toluene as solvent and triethylamine as a base. Examples of other representative analogs are listed in the Tables.

The reaction was also run with other phosphorodithioic acids (Examples 4–7) with hexane or toluene as solvents and with triethylamine or other similar base to remove the acid formed.

EVALUATION OF PRODUCTS

The additives were blended (1%) into solvent refined paraffinic neutral base stocks and tested for effectiveness as an antioxidant by Catalytic Oxidation Test and for antiwear activity in a standard 4-Ball Test machine. The conditions of the test, the results, and their comparison with the base oil are shown in Tables 1 and 2. The Oxidation Test and the 4-Ball Test are described in detail in U.S. Pat. No. 4,405,470 which is pertinent and is incorporated by reference.

TABLE 1

B-10 Catalytic Oxidation Test
325° F., 40 Hr.
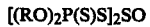

| Example No. | Additive (1%) | NN | KV % |
|---|---|---|---|
| 1 | None | 17.59 | 142.8 |
| 2 | R = 2-Ethylhexyl | 0.99 | 9.0 |
| 3 | R = 2-Ethylhexyl (No Solvent/No Base) | 0.71 | 12.5 |
| 4 | R = Oleyl | 2.54 | 14.9 |
| 5 | R = 4-Methyl-2-Pentyl | 2.9 | 32.5 |
| 6 | R = Butyl | 1.8 | 52.8 |
| 7 | R = Nonylphenyl | 1.8 | 48.5 |

TABLE 2

4-Ball Wear Test, 2,000 rpm,
60 Kg, 30 Mins, 1% Concentration

| Example No. | Additive (1%) | Wear Scar Diam (mm) 200° F. | 300° F. |
|---|---|---|---|
| 1 | None | 2.19 | — |
| 2 | R = Ethylhexyl | 0.96 | 0.80 |
| 3 | R = Ethylhexyl (No Base/No Solvent) | 0.94 | 1.58 |
| 4 | R = n-Butyl | 0.88 | 1.38 |
| 5 | R = 4-Methyl-2-Pentyl | 0.65 | 1.45 |
| 6 | R = Nonylphenyl | 0.70 | 1.03 |

The extreme degree of improvement over the basestock clearly demonstrates the claimed utility of additive lubricant products in accordance with the present invention.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A compound of the formula $[(RO)_2P(S)S]_2SO$ where R is hydrocarbyl having from 6 to about 32 carbon atoms and wherein hydrocarbyl is selected from aryl, aralkyl, alkaryl and cycloalkyl groups and wherein said aryl groups have from 6 to about 14 carbon atoms.

2. The compound of claim 1 wherein R is nonylphenyl.

3. A lubricant composition comprising a major amount of a lubricant and a minor antiwear/antioxidant amount of a compound of the formula $[(RO)_2P(S)S]_2SO$ where R is hydrocarbyl containing 1 to about 32 carbon atoms.

4. The composition of claim 3 where R is selected from the group consisting of alkyl, alkenyl, aryl, aralkyl, alkaryl and cycloalkyl where the aryl groups have from 6 to about 14 carbon atoms.

5. The composition of claim 3 where R is ethylhexyl.
6. The composition of claim 4 where R is oleyl.
7. The composition of claim 4 where R is 4-methyl-2-pentyl.
8. The composition of claim 4 where R is butyl.
9. The composition of claim 4 where R is nonylphenyl.
10. The composition of claim 3 wherein the lubricant is (1) a mineral oil, (2) a synthetic oil, (3) mixtures of (1) and (2).
11. The composition of claim 5 wherein the lubricant is (1) a mineral oil, (2) a synthetic oil, (3) mixtures of (1) and (2) or a grease prepared from either (1), (2) or (3).
12. The composition of claim 3 wherein the lubricant is a mineral oil.
13. The composition of claim 3 wherein the lubricant is a synthetic oil.
14. The composition of claim 3 wherein the lubricant is a mixture of a mineral oil and a synthetic oil.
15. A method of making a compound of the formula

where R is hydrocarbyl having from 6 to about 32 carbon atoms and wherein hydrocarbyl is selected from aryl, aralkyl, alkaryl and cycloalkyl wherein the aryl groups have from 6 to about 14 carbon atoms comprising reacting a dihydrocarbyl phosphorodithioic acid with a sulfurous oxyhalide in a molar ratio of from about 2.2:1 to about 2.5:1 under ambient conditions of temperature and pressure.

16. The method of claim 15 wherein R is nonylphenyl.

17. The method of claim 15 wherein the sulfurous-oxyhalide is selected from the group consisting of thionyl chloride and sulfuryl chloride.

18. The method of claim 16 wherein the sulfurous-oxyhalide is thionyl chloride.

* * * * *

UNITED STATES PATENT AND TRADEMARK OFFICE

Certificate

Patent No. 4,826,629            Patented: May 2, 1989

On petition requesting issuance of a certificate for correction of inventorship pursuant to 35 USC, it has been found that the above-identified patent, through error and without any deceptive intent, improperly sets forth the inventorship. Accordingly, it is hereby certified that the correct inventorship of this patent is:

Abraham O. M. Okorodudu
                         Robert E. Emhoffer
                         Angeline B. Cardis Signed and Sealed this Twenty-Second Day of August, 1989

WILLIAM R. DIXON, JR.
                                       *Supervisory Primary Examiner*
                                       *Patent Examing Group 110*